US012138252B2

(12) United States Patent
Tang-Liu et al.

(10) Patent No.: US 12,138,252 B2
(45) Date of Patent: *Nov. 12, 2024

(54) MULTIKINASE INHIBITORS OF VEGF AND TGF BETA AND USES THEREOF

(71) Applicant: AIVIVA BIOPHARMA, INC., Las Vegas, NV (US)

(72) Inventors: Diane Tang-Liu, Las Vegas, NV (US); Gerald Woodrow DeVries, San Clemente, CA (US)

(73) Assignee: AIVIVA BIOPHARMA, INC., Las Vegas, NV (US)

( * ) Notice: Subject to any disclaimer, the term of this patent is extended or adjusted under 35 U.S.C. 154(b) by 861 days.

This patent is subject to a terminal disclaimer.

(21) Appl. No.: 17/137,195

(22) Filed: Dec. 29, 2020

(65) Prior Publication Data

US 2021/0113535 A1   Apr. 22, 2021

Related U.S. Application Data

(62) Division of application No. 16/485,221, filed as application No. PCT/US2018/017810 on Feb. 12, 2018, now abandoned.

(60) Provisional application No. 62/457,929, filed on Feb. 12, 2017.

(51) Int. Cl.
| | |
|---|---|
| *A61K 31/4402* | (2006.01) |
| *A61K 9/00* | (2006.01) |
| *A61K 31/47* | (2006.01) |
| *A61K 31/496* | (2006.01) |
| *A61P 17/02* | (2006.01) |

(52) U.S. Cl.
CPC ........ *A61K 31/4402* (2013.01); *A61K 9/0014* (2013.01); *A61K 9/0019* (2013.01); *A61K 31/47* (2013.01); *A61K 31/496* (2013.01); *A61P 17/02* (2018.01)

(58) Field of Classification Search
CPC ............................ A61K 31/4402; A61P 17/02
See application file for complete search history.

(56) References Cited

U.S. PATENT DOCUMENTS

| | | | |
|---|---|---|---|
| 11,278,546 B2 * | 3/2022 | Tang-Liu | A61K 31/47 |
| 11,376,252 B2 * | 7/2022 | Tang-Liu | A61K 31/44 |
| 11,400,089 B2 * | 8/2022 | Tang-Liu | A61K 31/47 |
| 2006/0142373 A1 | 6/2006 | Park et al. | |
| 2008/0003219 A1 | 1/2008 | Peyman | |
| 2011/0190282 A1 | 8/2011 | Felding et al. | |
| 2013/0210733 A1 | 8/2013 | Morgans, Jr. et al. | |
| 2014/0323579 A1 | 10/2014 | Sheikh et al. | |
| 2017/0121323 A1 | 5/2017 | Liu et al. | |
| 2018/0222960 A1 | 8/2018 | Dubowchik et al. | |
| 2019/0255054 A1 | 8/2019 | Saiyed et al. | |
| 2019/0365737 A1 | 12/2019 | Haniuda et al. | |

FOREIGN PATENT DOCUMENTS

| | | |
|---|---|---|
| CN | 102209543 A | 10/2011 |
| CN | 104379129 A | 2/2015 |
| CN | 104379133 A | 2/2015 |
| CN | 108367165 A | 8/2018 |
| JP | 2008525370 A | 7/2008 |
| JP | 2013525398 A | 6/2013 |
| JP | 2013531067 A | 8/2013 |
| KR | 1020130069603 | 6/2013 |
| WO | 0040227 A2 | 7/2000 |
| WO | 2001002369 A2 | 1/2001 |
| WO | 2006067165 A2 | 6/2006 |
| WO | 2007053573 A2 | 5/2007 |
| WO | 2009137660 A2 | 11/2009 |
| WO | 2011134898 A1 | 3/2011 |
| WO | 2011060079 A1 | 5/2011 |
| WO | 2011064657 A2 | 6/2011 |
| WO | 2011147810 A1 | 12/2011 |
| WO | 2012012404 A1 | 1/2012 |
| WO | 2013188273 A1 | 12/2013 |
| WO | 2014078637 A1 | 5/2014 |
| WO | 2014086102 A1 | 6/2014 |
| WO | 2015005985 A1 | 1/2015 |
| WO | 2017062694 A1 | 4/2017 |
| WO | 2017210132 A1 | 12/2017 |
| WO | 2018022437 A2 | 2/2018 |

(Continued)

OTHER PUBLICATIONS

Enston-Newall, S., M21 Patient Stories: The Use of Novel Anti-Fibrotics, Pirfenidone and Nintedanib, in the Management of Idiopathic Pulmonary Fibrosis, IPF, Thorax, 72(Suppl 3), A247-A248, 2017.

Giddabasappa, A. et al., Axitinib inhibits retinal and choroidal neovascularization in in vitro and in vivo models, Experimental Eye Research, 145, 373-379, Apr. 2016.

International Search Report & Written Opinion, PCT/US2019/046401, mailed Nov. 15, 2019.

European Medicines Agency, Public Summary of Opinion on Orphan Designation, Riociguat for the Treatment of Systemic Sclerosis, Science Medicines Health, Aug. 2014.

Geschka, S. et al., Soluble Guanylate Cyclase Stimulation Prevents Fibrotic Tissue Remodeling and Improves Survival in Salt-Sensitive Dahl Rats, PLos One, vol. 6, Issue 7, e21853, 1-10, Jul. 2011.

(Continued)

*Primary Examiner* — Golam M Shameem
(74) *Attorney, Agent, or Firm* — Procopio, Cory, Hargreaves & Savitch LLP; Brent A. Johnson; Erica A. Spence

(57) ABSTRACT

A pharmaceutical composition for prevention or treatment of a disease or disorder characterized by chronic inflammation, with associated angiogenesis and fibrosis, wherein the disease or disorder is selected from the group consisting of rosacea, psoriasis, erythema multiforme, bullous pemphigoid, hereditary hemorrhagic telangiectasia, rheumatoid arthritis, atopic dermatitis, and dermal wound healing. The pharmaceutical composition includes at least one multikinase inhibitor selected from the group consisting of axitinib, nintedanib, and lenvatinib.

18 Claims, 3 Drawing Sheets

(56) References Cited

FOREIGN PATENT DOCUMENTS

| WO | 2018052053 A1 | 3/2018 |
|---|---|---|
| WO | 2018053010 A1 | 3/2018 |
| WO | 2018148653 A1 | 8/2018 |
| WO | 2018218116 A1 | 11/2018 |
| WO | 2019036367 A1 | 2/2019 |
| WO | 2020036993 A1 | 2/2020 |

OTHER PUBLICATIONS

International Search Report & Written Opinion, PCT/US2016/055865, mailed Dec. 20, 2016.
Kavian, N. et al., Sunitinib Inhibits the Phosphorylation of Platelet-Derived Growth Factor Receptor Beta in the Skin of Mice with Scleroderma-like Features and Prevents the Development of the Disease, Arthritis & Rheumatism, vol. 64, No. 6, 1990-2000, Jun. 2012.
Huang, J. et al., Nintedanib Ameliorates Fibrotic and Vascular Manisfestations in Preclinical Models of Systemic Sclerosis, Abstract No. 2153, Arthritis & Rheumatology, 67, 2584-2585, Oct. 2015.
Ota, Y. et al., Pirfenidone and BIBF1120 Suppress Collagen Synthesis in Skin Fibroblast from Patients with Systemic Sclerosis, Abstract No. 652, Arthritis & Rheumatism, 65, Oct. 2013.
European Search Report, Application No. 16854374.2, dated Jul. 24, 2019.
Kelly, R.J. et al., Axitinib—a selective inhibitor of the vascular endothelial growth factor (VEGF) receptor, Targeted Oncology, 4(4), 297-305, Dec. 2009.
Gerber, P.A. et al., Rosacea: the Cytokine and Chemokine Network, Journal of Investigative Dermatology Symposium Proceedings, 15(1), 40-47, Elsevier, Dec. 2011.
Gomaa, A.H.A. et al., Lymphangiogenesis and angiogenesis in non-phymatous rosacea, Journal of Cutaneous Pathology, 34(10), 748-753, Oct. 2007.
Ferrari, G. et al., Transforming Growth Factor-Beta 1 (TGF-Beta 1) Induces Angiogenesis Through Vascular Endothelial Growth Factor (VEGF)-Mediated Apoptosis, Journal of Cellular Physiology, 219(2), 449-458, May 2009.
Liu, Z. et al., VEGF and inhibitors of TGF Beta type-I receptor kinase synergistically promote blood-vessel formation by inducing alpha5-integrin expression, Journal of Cell Science, 122(18), 3294-3302, Sep. 2009.
Mikami, N. et al., Calcitonin gene-related peptide enhances experimental autoimmune encephalomyelitis by promoting Th17-cell functions. International Immunology, 24(11), 681-691, Nov. 2012.
Buhl, T. et al., Molecular and Morphological Characterization of Inflammatory Infiltrate in Rosacea Reveals Activation of Th1/Th17 Pathways, Journal of Investigative Dermatology, 135(9), 2198-2208, Sep. 2015.
Holmes, A.D. et al., Integrative concepts of rosacea pathophysiology, clinical presentation and new therapeutics, Experimental Dermatology, 26(8), 659-667, Aug. 2017.
Ferguson, M.W.J., et al., Scar-free healing: from embryonic mechanisms to adult therapeutic intervention, Phil Trans R Soc London B, 359, 839-850, 2004.
Han, G. et al., A Role for TGFBeta Signaling in the Pathogenesis of Psoriasis, J. Invest. Dermatol., 130, 371-377, 2010.
International Search Report & Written Opinion, PCT/US2018/017810, mailed May 8, 2018.
Johnson, A.K. et al., A quantitative real-time RT-PCR assay to measure TGF-Beta mRNA and its correlation with hematologic, plasma chemistry and organo-somatic indices responses in triamcinolone-treated Atlantic menhadden, Brevoortia tyrannus, Dev. Comp. Immunol., 30(5), 473-484, 2006.
Kim, M. et al., Recombinant erythroid differentiation regulator 1 inhibits both inflammation and angiogenesis in a mouse model of rosacea, Experimental Dermatology, 24, 680-685, 2015.
Lan, C.-C.E. et al., Tacrolimus abrogates TGF-Beta1-induced type I collagen production in normal human fibroblasts through suppressing p38MAPK signalling pathway: implications on treatment of chronic atopic dermatitis lesions, J. Eur. Acad. Dermatol. Venereol., 28, 204-215, 2014.
Pakyari, M. et al., Critical Role of Transforming Growth Factor Beta in Different Phases of Wound Healing, Advances In Wound Care, 2(5), 215-224, 2013.
Roskoski, Jr., R., Classification of small molecule protein kinase inhibitors based upon the structures of their drug-enzyme complexes, Pharmacological Research, Jan. 2016, Epub Oct. 31, 2015, vol. 103, pp. 26-48; Tables 1, 3, and 5.
Sakuma, M. et al., TGF-beta type I receptor kinase inhibitor down-regulates rheumatoid synoviocytes and prevents the arthritis induced by type II collagen antibody, International Immunology, Feb. 2007, Epub Nov. 29, 2006, vol. 19, No. 2, pp. 117-126.
Smith, J. R. et al., Expression of vascular endothelial growth factor and its receptors in rosacea, Br. J. Ophthalmol., 91, 226-229, 2007.
Yamasaki, K. et al., Increased serine protease activity and cathelicidin promotes skin inflammation in rosacea, Nature Medicine, 13, 975-980, 2007.
Yamasaki, K. et al., The molecular pathology of rosacea, J Dermatol Sci., 55(2), 77-81, 2009.
Antoniou, E.A. et al., Remission of psoriasis in a patient with hepatocellular carcinoma treated with sorafenib, in vivo, 30(5),677-680, Sep. 2016.
Ortiz-Ibanez, K. et al., Tofacitinib and other kinase inhibitors in the treatment of psoriasis, Actas Dermo-Sifiliográficas (English Edition), 104(4), 304-310, May 2013.
Kontzias, A. et al., Kinase inhibitors in the treatment of immune-mediated disease, F1000 Medicine Reports, 4, 2012.
Ng, C.Y. et al., Anticancer drugs induced severe adverse cutaneous drug reactions: an updated review on the risks associated with anticancer targeted therapy of immunotherapies, Journal of Immunology Research, Jan. 2018.
Lin, X. et al., New Anti-tumor Pharmacology, Jan. 2014.
Shi, Y. et al., Advances in Oncology in China, Oncologist Education in China, Jul. 2015.
Tsuzuki, T. et al., Tyrosine kinase inhibitor-induced vasculopathy in clear cell renal cell carcinoma: an unrecognized antitumour mechanism, Histopathology, 64(4), 484-493, Mar. 2014.
Jain, P. et al., Ponatinib as first-line treatment for patients with chronic myeloid leukaemia in chronic phase: a phase 2 study, The Lancet Haematology, 2(9), e376-e383, Sep. 2015.
European Search Report, Application No. 18751042.5, dated Nov. 17, 2020.
Yamaoka, H. et al., A novel small compound accelerates dermal wound healing by modifying infiltration, proliferation and migration of distinct cellular components in mice, Journal of Dermatological Science, 74(3), 204-213, Jun. 2014.
Weidemann, A.K. et al., Vascular endothelial growth factor inhibitors: investigational therapies for the treatment of psoriasis, Clinical, Cosmetic and Investigational Dermatology, 6, 233-244, 2013.
Sumiyoshi, K. et al., Transforming growth factor-beta1 suppresses atopic dermatitis-like skin lesions in NC/Nga mice, Clinical & Experimental Allergy, 32(2), 309-314, Feb. 2002.
Woo, Y.R. et al., Rosacea: Molecular Mechanisms and Management of a Chronic Cutaneous Inflammatory Condition, International Journal of Molecular Sciences, 17(9),1562, Sep. 2016.
U.S. Appl. No. 16/920,278, filed Jul. 2, 2020 First named Inventor: Diane Tang-Liu Assignee: AiViva BioPharma, Inc.
U.S. Appl. No. 17/267,938, filed Feb. 11, 2021 First named Inventor: Gerald Woodrow DeVries Assignee: AiViva BioPharma, Inc.
Extended European Search Report for European Application No. 198500415, dated Apr. 11, 2022.
Mir-Bonafe, J.M. et al., Improvement of actinic keratosis associated with sunitinib therapy for metastatic renal cell carcinoma, International Journal of Dermatology, 52(11), 1445-1447, Nov. 2013.
Williams, V.L. et al., Sorafenib-induced premalignant and malignant skin lesions, International Journal of Dermatology, 50(4), 396-402, Apr. 2011.
Liu, G. et al., Dynamic Contrast-Enhanced Magnetic Resonance Imaging As a Pharmacodynamic Measure of Response After Acute Dosing of AG-013736, an Oral Angiogenesis Inhibitor, in Patients

(56) References Cited

OTHER PUBLICATIONS

With Advanced Solid Tumors: Results From a Phase I Study, Journal of Clinical Oncology, 23(24), 5464-5473, Aug. 2005.

Wei, X. et al. "Efficacy of Lenvatinib, a multitargeted tyrosine kinase inhibitor, on laser-induced CNV mouse model of neovascular AMD" Experimental Eye Research (2018) vol. 168, pp. 2-11, (available online Dec. 25, 2017).

JAX Mice and Services, "Body Weight Information For C57BL/6J (000664)," Available online: URL: https://www.jax.org/jax-mice-and-services/strain-data-sheet-pages/body-weight-chart-000664, Accessed Aug. 19, 2022.

Stehle, F. et al., "Reduced Innunosuppressive Properties of Axitinib in Comparison with Other Tyrosine Kinase Inhibitors" Journal of Biological Chemistry, 288(23), 16334-16347, Jun. 2013.

Vaajanen, A. et al., "A Single Drop in the Eye—Effects on the Whole Body?" The Open Ophthalmology Journal, 11, 305-314, 2017.

\* cited by examiner

MULTIKINASE INHIBITORS OF VEGF AND TGF BETA AND USES THEREOF

FIELD OF INVENTION

This invention relates to methods of prevention and treatment of diseases or disorders characterized by chronic inflammation, with associated angiogenesis and fibrosis, such as psoriasis, rosacea, erythema multiforme, bullous pemphigoid, hereditary hemorrhagic telangiectasia, rheumatoid arthritis, atopic dermatitis, and dermal wound healing.

BACKGROUND OF THE INVENTION

Chronic inflammation, with associated angiogenesis and fibrosis, is a characteristic of many diseases, such as psoriasis, rheumatoid arthritis and rosacea. Although these broad pathologies are contributing factors, the underlying causes of such diseases are often not clear.

For example, the cause of rosacea, which is characterized by facial redness, dilated blood vessels on facial skin, papules, pustules, and swelling, remains unknown. What is known is whatever triggers episodes of flushing and blushing may play a part in the development of rosacea.

Similarly, psoriasis is an autoimmune disease characterized by patches of abnormal skin, which are typically red, itchy, and scaly. Such patches arise from abnormal, excessive growths of the skin. In psoriasis, skin cells are replaced every 3-5 days instead of every 28-30 days under normal conditions. These changes are believed to stem from the premature maturation of keratinocytes induced by an inflammatory cascade in the dermis. It is believed that these processes involve dendritic cells, macrophages, and T cells.

Because the pathophysiology of these diseases is complex and not completely understood, available treatment strategies are often not satisfactory. Kinase inhibitors, such as panatinib, pazopanib, regorafenib, could be proposed as treatment agents for these diseases. However, evidence of successful treatments with kinase inhibitors is lacking. Because of the lack of effective treatments, there is still a need for better treatments for such diseases.

SUMMARY OF THE INVENTION

One aspect of the invention relates to pharmaceutical compositions for prevention or treatment of a disease or disorder characterized by chronic inflammation, with associated angiogenesis and fibrosis. In accordance with embodiments of the invention, the disease or disorder may be selected from the group consisting of rosacea, psoriasis, erythema multiforme, bullous pemphigoid, hereditary hemorrhagic telangiectasia, rheumatoid arthritis, atopic dermatitis, and dermal wound healing. In accordance with embodiments of the invention, a pharmaceutical composition may include at least one multi-kinase inhibitor selected from the group consisting of axitinib, nintedanib, and lenvatinib.

One aspect of the invention relates to methods of prevention and treatment of a disease or disorder characterized by chronic inflammation, with associated angiogenesis and fibrosis. A method in accordance with one embodiment of the invention comprises administering an effective amount of a multikinase inhibitor to a subject in need thereof. The multikinase inhibitors are selected from axitinib, nintedanib, and lenvatinib. The disease or disorder is selected from the group consisting of rosacea, psoriasis, erythema multiforme, bullous pemphigoid, hereditary hemorrhagic telangiectasia, rheumatoid arthritis, atopic dermatitis, and dermal wound healing.

In accordance with embodiments of the invention, the administering is by a topical formulation, intralesional injection, paralesional injection, or by intra-tissue injection. The topical formulation is selected from a cream, an ointment, a solution, an emulsion, a medical plaster, or a local delivery form.

Other aspect of the invention would become apparent with the following detailed description and the attached drawings.

DETAILED DESCRIPTION

Figure 1:
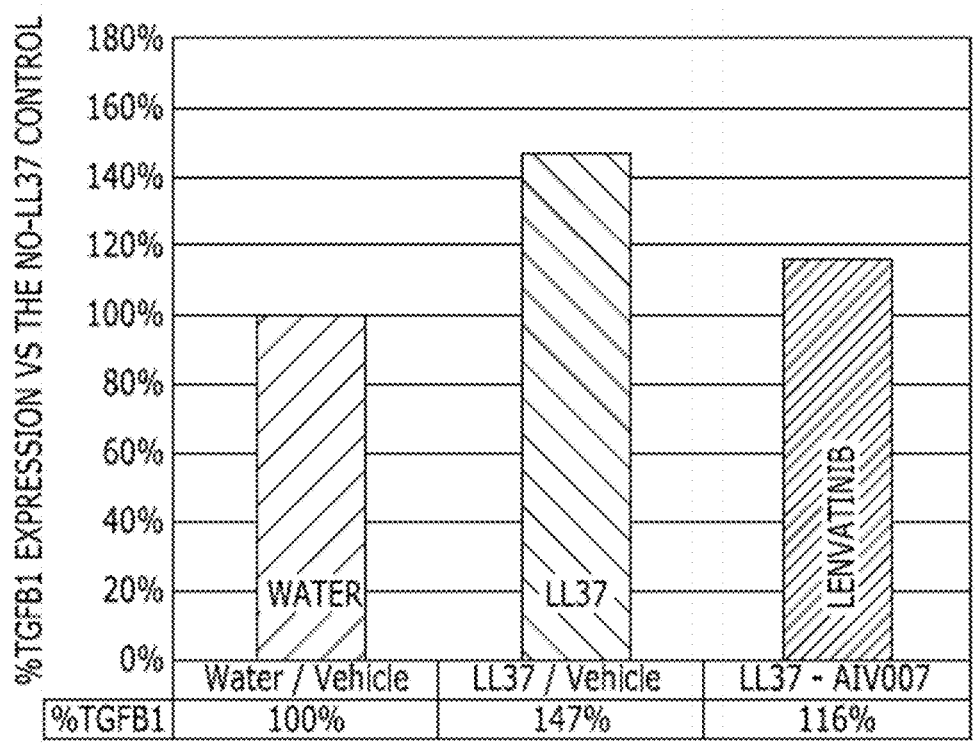
FIG. 1 shows TGFb1 mRNA expression levels for mice treated with water and vehicle, mice induced with LL37 and vehicle, and mice induced with LL37 and treated with Lenvatinib. The TGFb1 mRNA expression level in mice without LL37 induction is set as 100%. AIV007 is lenvatinib.

Embodiments of the invention relate to compounds, compositions and methods for the treatment or prevention of diseases or disorders associated with chronic inflammation, which is often accompanied with angiogenesis and/or fibrosis. In particular, embodiments of the invention relate to the prevention, or treatment, of rosacea in humans. Compounds of the invention possess a certain spectrum of multi-kinase inhibition activities (i.e., these multi-kinase inhibitors can inhibit multiple kinases) that affect certain growth factor and cytokine signaling pathways, such as vascular endothelial growth factor (VEGF), transforming growth factor beta (TGF beta), platelet-derived growth factor (PDGF), and fibroblast growth factor (FGF).

Many diseases (e.g., psoriasis, rheumatoid arthritis, and rosacea) are associated with chronic inflammation and angiogenesis. However, the mechanisms responsible for many of these diseases are complex and not well understood. As a result, treatments of these diseases often are not satisfactory.

Rosacea affects approximately 5-10% of the adult population in the United States. Pharmacological agents currently approved for topical treatments of rosacea include sodium sulfacetamide, azelaic acid, metronidazole, and the alpha-adrenergic agonist brimonidine. Off-label uses of topical retinoids, calcineurin inhibitors, macrolides, benzoyl peroxide, permethrin or ivermectin has also been shown to be somewhat beneficial. The need for new pharmaceutical strategies, however, is clear and the development of emerging therapies is ongoing.

Regulation of inflammation and angiogenesis in these diseases is dependent on a complex network of growth factors and cytokines, and their signaling pathways. Vascular endothelial growth factor (VEGF) is a major stimulator of angiogenesis and has inflammatory activities. It has been reported that VEGF and its receptors VEGFR-1 and VEGFR-2 are upregulated in rosacea (Smith, J R et al., Br. J. Ophthalmol. 91:226-229, 2007). Furthermore, TGF beta has been shown to be an important regulator of chronic inflammation in diseases such as psoriasis and atopic dermatitis (Han, G et al., J. Invest. Dermatol. 13: 371-377, 2010; Lan, C C et al. J. Eur. Acad. Dermatol. Venereol. 28: 204-215, 2014). These findings indicate that compounds that can modulate multiple regulatory factors may be more effective for the treatments of such diseases.

Inventors of the present invention have found that compounds having multi-kinase inhibitor activities with a selective profile can serve as novel agents for the prevention, treatment and modulation of rosacea and other skin diseases characterized by chronic inflammation and angiogenesis. Tests of these multi-kinase inhibitors reveal that these compounds indeed are effective in the treatment and control of these diseases that involve inflammation, and associated angiogenesis and/or fibrosis.

In accordance with embodiment of the invention, a method may involve administering a multi-kinase inhibitor to a subject in need of treatments or prevention of diseases associated with angiogenesis, inflammation and/or fibrosis. The multi-kinase inhibitors may include, but are not limited to, axitinib, nintedanib and lenvatinib and their stereoisomer, tautomer, prodrug, free base, analogs, metabolites, pharmaceutically acceptable salt, solvate or solvate of a salt thereof.

As used herein, a "pharmaceutically acceptable salt" refer to a compound that has been modified by adding an acid or base to make a salt thereof, wherein the compound may be a parent compound, or a prodrug, a derivative, a metabolite, or an analog of the parent compound.

In accordance with embodiments of the invention, the diseases or disorders characterized by chronic inflammation, with associated angiogenesis and fibrosis, include but not limited to rosacea, psoriasis, erythema multiforme, bullous pemphigoid, hereditary hemorrhagic telangiectasia, rheumatoid arthritis, atopic dermatitis and dermal wound healing.

In accordance with embodiments of the invention, compounds of the present invention may be administered by intralesional, paralesional, or intra-tissue injection. Compounds may also be administered orally (e.g., capsules, sustained release capsules, tablets, sustained release tablets, chewable tablets, sublingual tablets, effervescent tablets, pills, suspensions, powders, granules, etc.). Compounds of the present invention may also be administered by topical formulations (e.g., cream, ointment, solution, emulsion, medical plaster, local delivery forms, etc.).

In accordance with embodiments of the invention, compounds of the present invention may be used in conjunction with any of the vehicles and excipients commonly employed in pharmaceutical preparations including polymers.

Embodiments of the present invention will be illustrated with the following examples. One skilled in the art would appreciate that these examples are for illustration only and are not intended to limit the scope of the invention because one skilled in the art would appreciate that modifications and variations are possible without departing from the scope of the invention.

EXAMPLE 1

The Compounds of Invention Reduce Derma Inflammation in Mice After LL-37 Challenge Recent studies show a link between triggers of rosacea (including Demodex folliculorum, UV radiation, stress, etc.) and induced cellular and tissue responses. It has been suggested that an altered innate immune response is involved in the disease pathogenesis (Yamasaki, K and Gallo, R., J Dermatol Sci., 55: 77-81, 2009)

Triggering the innate immune system normally results in a controlled increase in cytokines and antimicrobial peptides, such as cathelicidins, in the skin. Some forms of cathelicidin peptides have the capacity to be both proinflammatory and vasoactive. Individuals with rosacea not only express high levels of cathelicidin, but also produce forms of cathelicidin peptides which promote leukocyte chemotaxis, angiogenesis, and expression of extracellular matrix components. It has been shown that injection of these peptides into the skin of mice results in skin inflammation resembling pathological changes seen in rosacea patients. A cathelicidin derived peptide LL-37 has been used to induce rosacea-like responses in mice. (Yamasaki, K. et al., Nature Medicine 13: 975-980, 2007; Kim, M. et al., Experimental Dermatology 24: 680-685, 2015).

In our study, mice were injected subcutaneously with 40 μL of LL-37 (3.3 mg/mL) to induce inflammatory reactions. Immediately following the LL-37 injection, axitinib, nintedanib, and lenvatinib were individually administered as a single intradermal injection (1.6 mg). LL-37 injection was repeated every 12 hours for a total of 4 injections. Endotoxin-free water and dexamethasone (3 mg/kg by intraperitoneal injection, twice), respectively, were used as negative and positive control groups.

At 48 hours after the initial LL-37 injection, the dorsal skin was photographed, and the severity of skin lesions were scored for redness and measured for areas of involvement.

Mice were then anaesthetized, and tissue samples of lesion sites were excised and fixed for H&E stainings and immunohistochemical analysis. Markers for inflammation (CD4 and CD8) were determined using specific antibodies. TGF beta levels are measured by mRNA expression using qPCR.

As shown in FIG. 1, among all treatment groups, lenvatinib (AIV007) showed the lowest TGFb-1 mRNA expression. The TGFb1 mRNA expression in mice induced with LL37 and treated with lenvatinib was 79% of that challenged with LL37 alone (i.e., without treatment).

Figure 2:
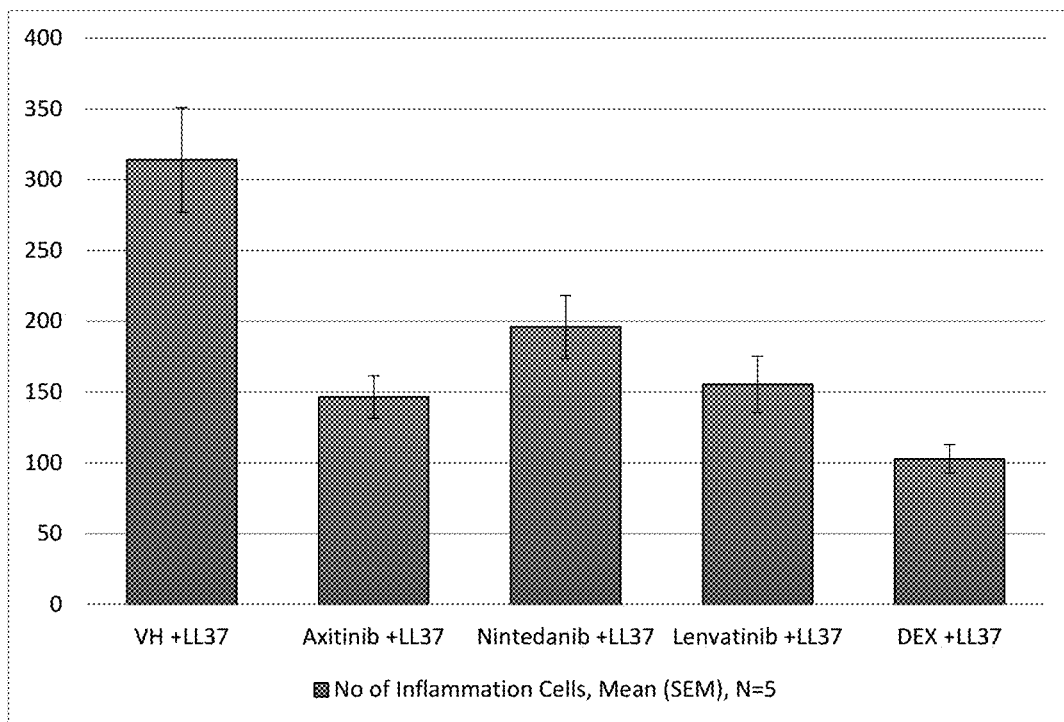
FIG. 2 shows inflammation scores of treatment groups with intradermal LL37 induction in mice.

The tissue samples were analyzed for inflammation characteristics. Histopathology endpoints included inflammation, and CD4+ and CD8+ T-lymphocyte immunostaining. For inflammation scores, tissues were examined histologically and scored for inflammatory cell infiltrate. As shown in FIG. 2, Axitinib, nintedanib, and lenvatinib showed prominent reductions in the scores of inflammation. These results indicate that the multi-kinase inhibitors of the invention will be effective therapeutic agents for preventing or treating diseases that are caused by or associated with inflammation, such as rosacea, psoriasis, and rheumatoid arthritis.

Figure 3:
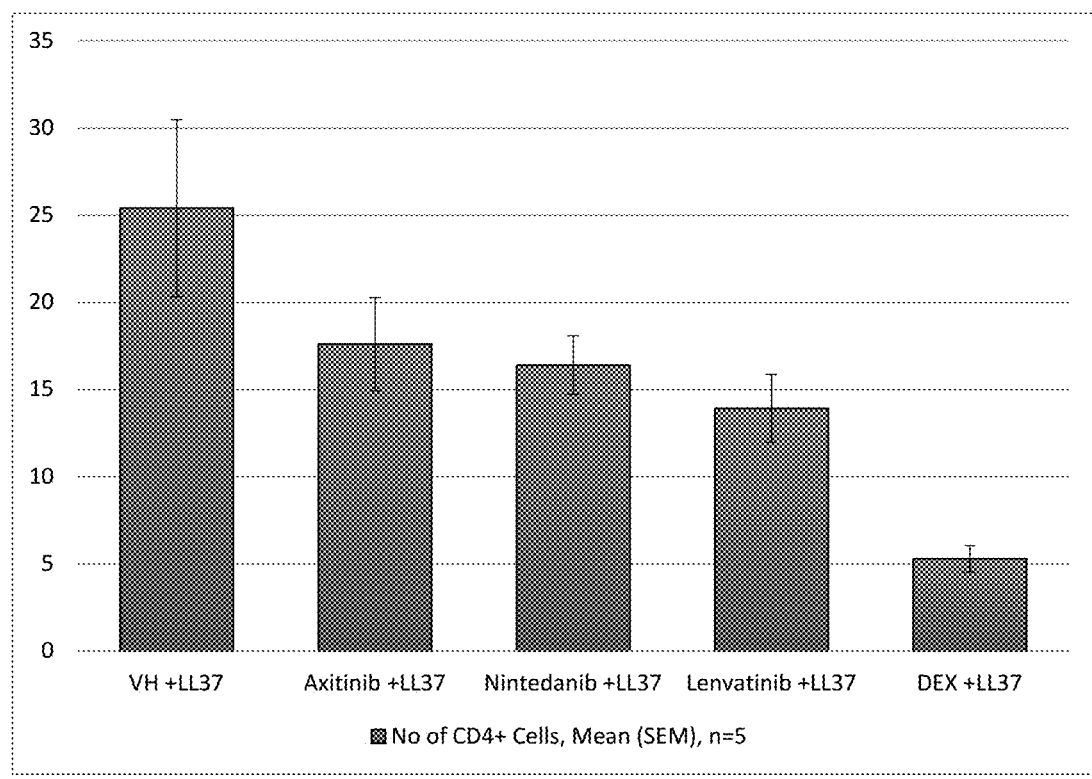
FIG. 3 shows CD4+ Lymphocyte Scores after treatments with multikinase inhibitors of the invention in intradermal LL37 injection-induced inflammation model in mice.

As shown in FIG. 3, multi-kinase inhibitors of the invention, axitinib, nintedanib, and lenvatinib, are also effective in the reduction of CD4+ lymphocyte scores in the mice model of inflammation induced by intradermal LL37 injections. The reductions range from about 30% to about 40%.

Figure 4:
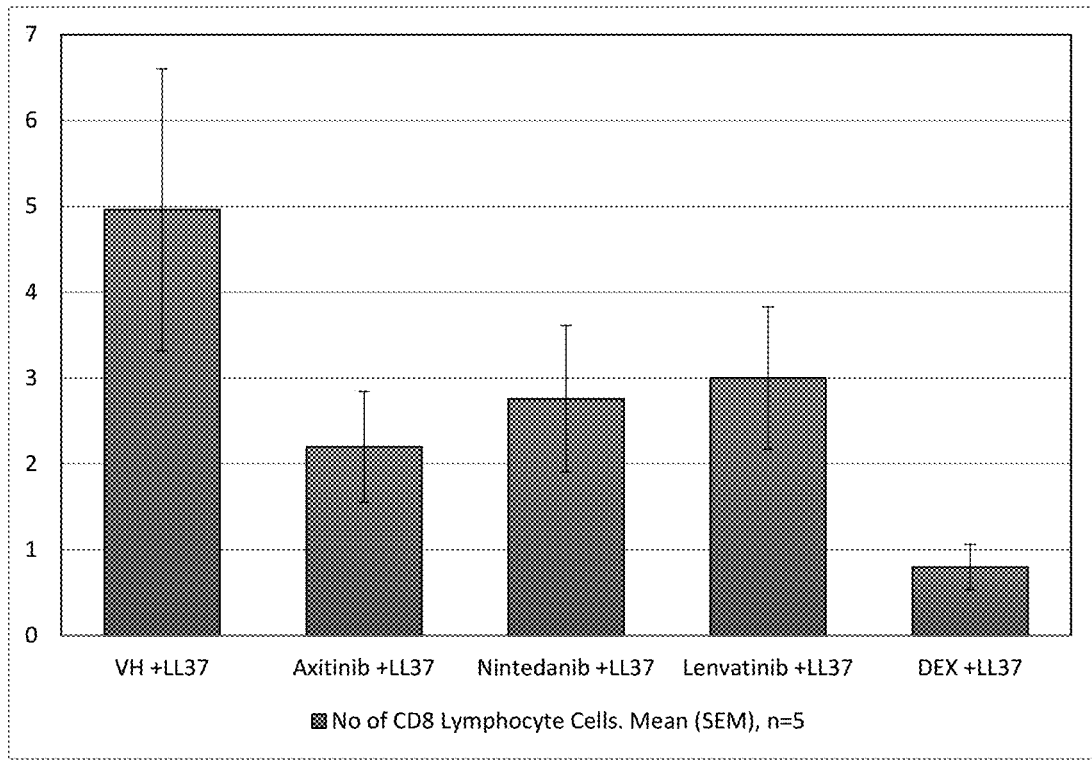
FIG. 4 shows CD8+ Lymphocyte Scores after treatments with multikinase inhibitors of the invention in intradermal LL37 injection-induced inflammation model in mice.

Similarly, as shown in FIG. 4, multi-kinase inhibitors of the invention, axitinib, nintedanib, and lenvatinib, are also effective in the reduction of CD8+ lymphocyte scores in the mice model of inflammation induced by intradermal LL37 injections. The reductions range from about 40% to about 55%.

In summary, compounds of the invention demonstrated inhibitory effects in LL37-induced inflammation. In addition, these compounds also regulate TGF beta mRNA expression. These results support the notion that these compounds possess an inhibitory profile necessary for the prevention and treatment of diseases characterized by chronic inflammation, such as rosacea, atopic dermatitis, psoriasis, and rheumatoid arthritis.

EXAMPLE 2

Compounds of the Invention Reduce Dermal Levels of TGFb1 Following Wound-Induced Inflammation in Minipigs The purpose of this study was to evaluate the topical effects of axitinib, nintedanib, sorafenib and lenvatinib when administered via intradermal injection to the dorsal skin along linear incisions of minipigs. Linear incisional wound was made to elicit inflammatory and wound healing process in the skin. After dosing, animals were observed postdose for 9 days to assess the levels of TGFb1 expressions in the skin.

Three male Gottingen Minipigs® dosed once via intradermal injection along the edges of each of the linear incision wound sites for each animal (wounds on the dorsum, perpendicular to the spine, approximately 3 cm in length and 3 cm distance from the spine). Each incisional wound received approximately 16 mg of the test compound intradermally once along both sides of the linear wound.

On days of 4, 7, and 9 post-dosing, one 4 mm dermal punch biopsy was collected for each incisional wound and processed for TGF-beta 1 analysis with ELISA, using a commercial kit (e.g., the kit from Thermo Fisher or other vendors). The effects of these test compounds on the dermal expression levels of TGFb1 are shown in FIG. 5.

Figure 5:
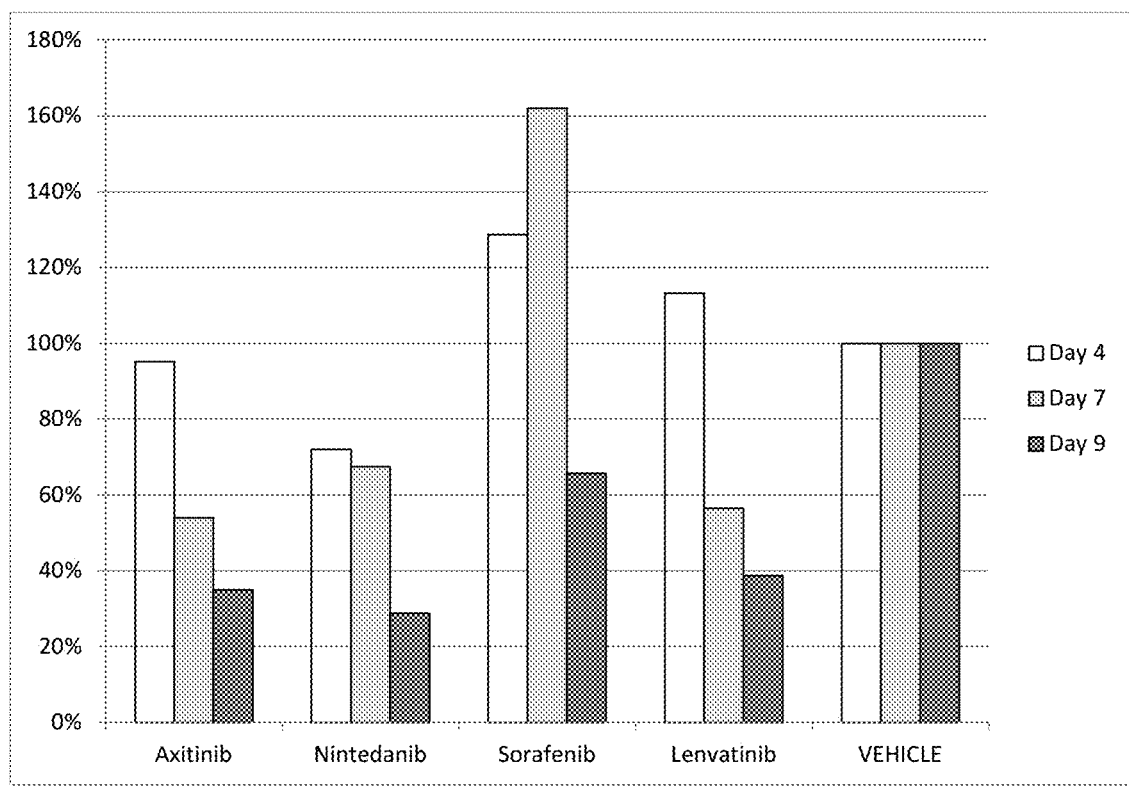
FIG. 5 shows the effects of compounds of the invention on TGFb1 expressions over time following wounding and drug treatments.

As shown in FIG. 5, the multi-kinase inhibitors of the invention, axitinib, nintedanib, and lenvatinib, are very effective in suppressing the expression of TGF beta 1 in a time-dependent manner. In contrast, another kinase inhibitor, sorafenib, is not as effective. These results indicate that not all kinase inhibitors are equal and that multi-kinase inhibitors having a specific spectrum of kinase inhibition are needed for methods of the invention.

Multiple growth factors and cytokines have been shown to regulate dermal inflammation and wound healing. TGF-beta1 and TGFbeta2, in particular, are important in all phases of the wound healing process (Pakyari M. et al. Advances in Wound Care, 2: 215-224, 2013). The inhibition of TGFbeta1 levels in this wound healing and inflammation study by axitinib, nintedanib, and lenvatinib strongly suggests therapeutic roles for these multi-kinase inhibitors in the regulation of dermal inflammation. Inhibition of TGF-beta1 by axitinib, nintedanib, and lenvatinib are especially important for chronic inflammatory diseases given that previous studies have demonstrated that blocking TGF beta signaling has a positive effect in animal models of psoriasis and atopic dermatitis (Han G, et al., J Invest Dermatol 130: 371-377, 2010.; Lan C C, et al. J Eur Acad Dermatol Venereol 28: 204-215, 2014).

Furthermore, inhibitions of TGF beta1 early in the wound healing response by these multi-kinase inhibitors (days 7 & 9) parallel previous findings, in which early application of neutralizing antibodies to TGF beta 1 & 2 during dermal wound healing produced the best outcome (Ferguson M W and O'Kane S, Phil Trans R Soc London B 359: 839-850, 2004). These observations would suggest that axitinib, nintedanib, and lenvatinib are expected to provide better therapeutic values than other multi-kinase inhibitors, such as sorafenib, whose inhibitory profile is delayed in this dermal wound healing model.

EXAMPLE 3

Compounds of the Invention Reduce the Expression of TGF Beta in a Rabbit Ear Injury Model The objective of this study was to examine the effect of test compounds on wound healing and TGF beta expression after dermal injury in a rabbit ear hypertrophic scar model.

In New Zealand white rabbits, maintained under a surgical plane of anesthesia, trauma stimulation of the skin on the ventral surface of both ears is initiated on Day 1. Trauma sites are evaluated on Days 8, 15, 22, 29, 36, and 43. On days 15 and 29, each site is dosed with test compounds (e.g., 1% w/w, 100 µl) by intradermal or intralesional injections.

Animals are euthanized on Day 43, and the trauma sites are harvested and frozen for TGF beta analysis using quantitative RT-PCR (qRT-PCR) (e.g., A. K. Johnson et al., Dev. Comp. Immunol., 2006; 30(5): 473-84). TGF beta1 mRNA expression levels in treated trauma samples are compared to the expression level in the untreated trauma sample.

Figure 6:
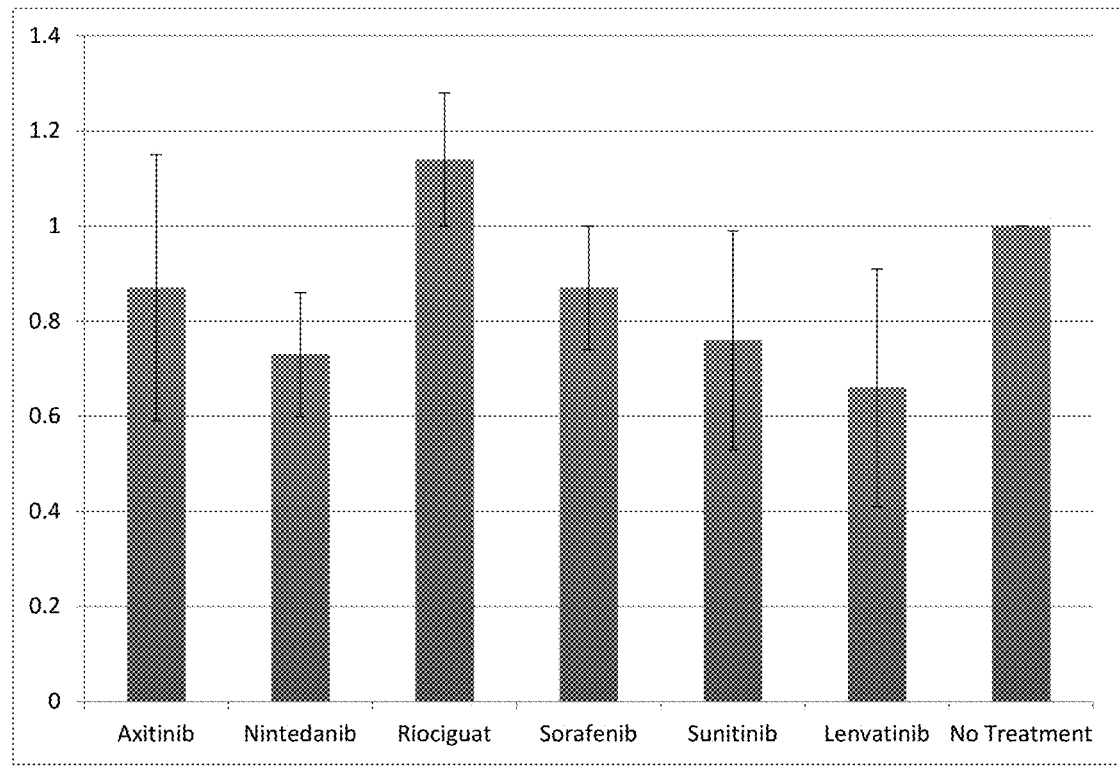
FIG. 6 shows folds of TGF-β1 mRNA expressions in rabbit ear wound sites after intradermal treatments with multi-kinase inhibitors of the invention, as compared to the untreated wound site.

As shown in FIG. 6, the mean folds of TGF beta mRNA expression in axitinib, nintedanib, sorafenib, sunitinib, and lenvatinib-treated samples are lower than the expression level in the untreated wound sample.

At necropsy, each treatment site was harvested and preserved for hematoxylin and erosion and Mason's trichrome stainings. Each lesion was examined histologically and graded for neovascularization, fibrosis and re-epithelialization using a five-step/severity grading system (minimal, mild, moderate, marked, and severe). The average total score is an aggregation of these microscopic findings relating to an inflammatory response. The histopathology data for axitinib and nintedanib-treated trauma sites show decreased angiogenesis and fibrosis, as revealed by these stainings. In contrast, samples from sorafenib or sunitinib do not show any reduction in angiogenesis.

Axitinib (Table 2) had less neovascularization than untreated wounds. The average total score of the test wounds was 1.4 lower than the untreated wounds. The histopathology data for axitinib treated trauma sites show decreased angiogenesis and fibrosis.

TABLE 2

Histopathology Findings of Rabbit Ear Wound Treated with Intradermal Dosing of 1% Axitinib

|  | Neovascularization | Fibrosis/Collagen | Re-epithelialization | Total Score |
| --- | --- | --- | --- | --- |
| Treated Mean | 1 | 3.3 | 0.3 | 4.6 |
| Untreated Control | 3 | 3 | 0 | 6 |

Nintedanib (Table 3) produced much less neovascularization and about the same fibrosis as untreated wounds. The average total score of the test wounds was 1.5 lower than untreated wounds. Overall, the test sites have less scar formation, as compared with the control sites.

TABLE 3

Histopathology Findings of Rabbit Ear Wound Treated with Intradermal Dosing of 1% w/w Nintedanib

|  | Neovascularization | Fibrosis/ Collagen | Re-epithelialization | Total Score |
|---|---|---|---|---|
| Treated Mean | 1 | 3 | 0.5 | 4.5 |
| Untreated Control | 3 | 3 | 0 | 6 |

Sorafenib (Table 4) produced slightly increased neovascularization and similar, or increased fibrosis, as compared to the control sites. Overall, the test compound does not appear to have reduced scar formation, as compared to the untreated wound sites.

TABLE 4

Histopathology Findings of Rabbit Ear Wound Treated with Intradermal Dosing of 1% w/w Sorafenib

|  | Neovascularization | Fibrosis/ Collagen | Re-epithelialization | Total Score |
|---|---|---|---|---|
| Treated Mean | 3 | 2.5 | 0.3 | 5.8 |
| Untreated Control | 2 | 2 | 0 | 4 |

These data support the fact that compounds of invention possess a certain spectrum of multi-kinase inhibition activities necessary to treat diseases and disorders characterized by angiogenesis, fibrotic repair, and inflammation. The certain spectrum of multi-kinases may be involved in the signaling pathways of VEGF and TGF beta.

The above data demonstrates that axitinib, nintedanib and lenvatinib are able to significantly reduce inflammation in a well-recognized animal model of rosacea. Furthermore, in the animal model, axitinib, nintedanib and lenvatinib inhibited the tissue infiltration of CD4+ and CD8+ T-lymphocytes, contributors of innate immune responses related to the pathogenesis of rosacea. In addition, the regulatory profiles of axitinib, nintedanib and lenvatinib in modulating growth factors and cytokines, such as PDGF, VEGF and TGF beta, support their roles as effective therapeutic agents for chronic dermal inflammatory diseases, such as rosacea, psoriasis and atopic dermatitis.

What is claimed is:

1. A method of treating a disease or disorder, comprising administering at least one multikinase inhibitor to a mammal in need thereof, wherein the disease or disorder is rosacea, psoriasis, or atopic dermatitis, wherein the multikinase inhibitor is axitinib, nintedanib, lenvatinib, or a combination thereof.

2. The method of claim 1, wherein the multikinase inhibitor is axitinib.

3. The method of claim 1, wherein the multikinase inhibitor is nintedanib.

4. The method of claim 1, wherein the multikinase inhibitor is lenvatinib.

5. The method of claim 1, wherein the disease or disorder is rosacea.

6. The method of claim 1, wherein the disease or disorder is psoriasis.

7. The method of claim 1, wherein the disease or disorder is atopic dermatitis.

8. The method of claim 1, wherein the administering is by a topical formulation, intralesional injection, paralesional injection, or by intra-tissue injection.

9. The method of claim 8, wherein the administering is by a topical formulation.

10. The method of claim 9, wherein the topical formulation comprises a cream, an ointment, a solution, an emulsion, a medical plaster, a local delivery form, or a combination thereof.

11. The method of claim 9, wherein the topical formulation comprises a cream.

12. The method of claim 9, wherein the topical formulation comprises an ointment.

13. The method of claim 9, wherein the topical formulation comprises a solution.

14. The method of claim 9, wherein the topical formulation comprises an emulsion.

15. The method of claim 9, wherein the topical formulation comprises a medical plaster.

16. The method of claim 8, wherein the administering is by intralesional injection.

17. The method of claim 8, wherein the administering is by paralesional injection.

18. The method of claim 1, wherein the mammal is a human being.

* * * * *